(12) United States Patent
Singh

(10) Patent No.: US 12,251,262 B2
(45) Date of Patent: Mar. 18, 2025

(54) VASCULAR DEVICE INSERTION SYSTEM AND APPARATUS

(71) Applicant: Bard Peripheral Vascular, Inc., Franklin Lakes, NJ (US)

(72) Inventor: Aseem Singh, Tempe, AZ (US)

(73) Assignee: Bard Peripheral Vascular, Inc., Franklin Lakes, NJ (US)

( * ) Notice: Subject to any disclaimer, the term of this patent is extended or adjusted under 35 U.S.C. 154(b) by 328 days.

(21) Appl. No.: 17/906,915

(22) PCT Filed: Mar. 31, 2020

(86) PCT No.: PCT/US2020/025879
§ 371 (c)(1),
(2) Date: Sep. 21, 2022

(87) PCT Pub. No.: WO2021/201835
PCT Pub. Date: Oct. 7, 2021

(65) Prior Publication Data
US 2023/0112959 A1    Apr. 13, 2023

(51) Int. Cl.
*A61B 8/00* (2006.01)
*A61B 8/12* (2006.01)
(Continued)

(52) U.S. Cl.
CPC .............. *A61B 8/42* (2013.01); *A61B 8/12* (2013.01); *A61B 8/445* (2013.01); *A61M 25/0097* (2013.01); *A61M 25/0113* (2013.01)

(58) Field of Classification Search
None
See application file for complete search history.

(56) References Cited

U.S. PATENT DOCUMENTS

| | | |
|---|---|---|
| 4,854,325 A | 8/1989 | Stevens |
| 5,524,635 A | 6/1996 | Uflacker et al. |

(Continued)

FOREIGN PATENT DOCUMENTS

| | | |
|---|---|---|
| CN | 102462510 B | 5/2012 |
| CN | 107961077 B | 7/2024 |

(Continued)

OTHER PUBLICATIONS

Chinese Office Action for Appln. No. 202080099278.2, mailed Sep. 9, 2024, 22 pages.

(Continued)

*Primary Examiner* — Joseph M Santos Rodriguez
(74) *Attorney, Agent, or Firm* — Dinsmore & Shohl LLP (57) ABSTRACT

A vascular device insertion system includes a support catheter having a hub, a flexible elongate member that extends distally from the hub, and a catheter lumen that extends through the hub and the flexible elongate member. An insertion module housing is configured to contain a motor having a hollow motor shaft. The hollow motor shaft has a proximal end, a distal end, a distal end portion, and an elongate opening that extends from the proximal end to the distal end. The distal end portion of the hollow motor shaft is configured to couple to the hub of the support catheter. The elongate opening of the hollow motor shaft and the catheter lumen of the support catheter together define a continuous passage. A motor controller is electrically coupled to the motor, and is configured to rotationally oscillate the hollow motor shaft to in turn rotationally oscillate the support catheter.

20 Claims, 2 Drawing Sheets

(51) Int. Cl.
    *A61M 25/00* (2006.01)
    *A61M 25/01* (2006.01)

(56) References Cited

U.S. PATENT DOCUMENTS

| | | | |
|---|---|---|---|
| 5,908,395 | A | 6/1999 | Stalker et al. |
| 8,425,465 | B2 | 4/2013 | Nagano et al. |
| 8,926,529 | B2 | 1/2015 | Rollins et al. |
| 9,050,438 | B2 | 6/2015 | Rollins et al. |
| 10,092,731 | B2 | 10/2018 | Almansouri et al. |
| 10,159,819 | B2 | 12/2018 | Duffy et al. |
| 2007/0083081 | A1 | 4/2007 | Schlagenhauf et al. |
| 2007/0270755 | A1 | 11/2007 | Von Oepen et al. |
| 2015/0073339 | A1 | 3/2015 | Pacheco et al. |
| 2015/0335348 | A1 | 11/2015 | Cohen et al. |
| 2017/0043137 | A1 | 2/2017 | Felkins et al. |
| 2018/0317952 | A1 | 11/2018 | Jamous et al. |

FOREIGN PATENT DOCUMENTS

| | | |
|---|---|---|
| EP | 1774913 A1 | 4/2007 |
| JP | 08126646 A | 5/1996 |
| JP | 2012526606 A | 11/2012 |
| JP | 2015524315 A | 8/2015 |
| JP | 2018500133 A | 1/2018 |
| WO | 9716126 A1 | 5/1997 |
| WO | 2010132147 A1 | 11/2010 |
| WO | 2014022716 A2 | 2/2014 |
| WO | 2016108860 A1 | 7/2016 |

OTHER PUBLICATIONS

Xin Nan, Ultrasound Cardiogram Diagnosis in Clinical Common Cardiovascular Diseases and Functions, pp. 168-169, Gansu Science & Technology Press, Nov. 30, 2005.
International Search Report and Written Opinion dated Dec. 17, 2020, in International Application No. PCT/US2020/025879.
Japanese Office Action dated Nov. 17, 2023 pertaining to Japanese application No. 2022-559515 filed Sep. 29, 2022, pp. 1-4.

VASCULAR DEVICE INSERTION SYSTEM AND APPARATUS

CROSS-REFERENCE TO RELATED APPLICATIONS

This application is a U.S. National Phase of International Application No. PCT/US2020/025879, entitled "VASCULAR DEVICE INSERTION SYSTEM AND APPARATUS" and filed Mar. 31, 2020, which is incorporated herein by reference in its entirety.

TECHNICAL FIELD

The present invention relates to vascular interventional devices, and, more particularly, to a vascular device insertion system and apparatus.

BACKGROUND ART

Some vascular procedures require a placement of a guidewire in a blood vessel as an initial step in the vascular procedure. However, at times it may be difficult for the physician to manually manipulate the guidewire through a blood vessel, such as in regions where the blood vessel is partially or totally occluded.

What is needed in the art is a vascular device insertion system and apparatus, which may be used to aid in the insertion and placement of a guidewire and/or a vascular catheter in a blood vessel.

SUMMARY OF INVENTION

The present invention provides a vascular device insertion system and apparatus, which may be used to aid in the insertion and placement of a guidewire and/or a vascular catheter in a blood vessel.

The invention, in one form, is directed to a vascular device insertion system. The system includes a support catheter, an insertion module housing containing a motor, and a motor controller. The support catheter has a hub, a flexible elongate member that extends distally from the hub, and a catheter lumen that extends through the hub and the flexible elongate member. The motor has a hollow motor shaft arranged along a longitudinal axis. The hollow motor shaft has a proximal end, a distal end, a distal end portion, and an elongate opening that extends from the proximal end to the distal end along the longitudinal axis. The distal end portion of the hollow motor shaft is configured to couple to the hub of the support catheter. The elongate opening of the hollow motor shaft and the catheter lumen of the support catheter together define a continuous passage. The motor controller is electrically coupled to the motor. The motor controller is configured to control the motor so as to rotationally oscillate the hollow motor shaft about the longitudinal axis and to in turn rotationally oscillate the support catheter.

The invention, in another form, is directed to a vascular device insertion system. The system includes a support catheter, an insertion module housing containing a motor, a guidewire, and a motor controller. The support catheter has a hub, a flexible elongate member that extends distally from the hub, and a catheter lumen that extends through the hub and the flexible elongate member. The motor has a hollow motor shaft arranged along a longitudinal axis. The hollow motor shaft has a proximal end, a distal end, a distal end portion, and an elongate opening that extends from the proximal end to the distal end along the longitudinal axis. The distal end portion of the hollow motor shaft is configured to couple to the hub of the support catheter. The elongate opening of the hollow motor shaft and the catheter lumen of the support catheter together define a continuous passage. The guidewire has a first end and a second end. The guidewire is located in the continuous passage defined by the elongate opening in the hollow motor shaft and the catheter lumen of the support catheter, wherein a first end portion of the guidewire is proximal to the proximal end of the hollow motor shaft. The continuous passage is configured such that the guidewire is freely manually movable in the continuous passage by manual manipulation of the first end portion of the guidewire. The motor controller is electrically coupled to the motor. The motor controller is configured to rotationally oscillate the hollow motor shaft about the longitudinal axis to in turn rotationally oscillate the support catheter.

The invention, in still another form, is directed to a vascular device insertion apparatus for use in advancing a support catheter and a guide wire in a vessel. The support catheter has a hub, a flexible elongate member that extends distally from the hub, and a catheter lumen that extends through the hub and the flexible elongate member. The vascular device insertion apparatus includes an insertion module housing that is configured to contain a motor that has a hollow motor shaft arranged along a longitudinal axis. The hollow motor shaft has a proximal end, a distal end, a distal end portion, and an elongate opening that extends from the proximal end to the distal end along the longitudinal axis. The distal end portion of the hollow motor shaft is configured to couple to the hub of the support catheter. The elongate opening of the hollow motor shaft and the catheter lumen of the support catheter together define a continuous passage. The continuous passage is configured to receive the guidewire. The motor controller is electrically coupled to the motor. The motor controller is configured to rotationally oscillate the hollow motor shaft about the longitudinal axis to in turn rotationally oscillate the support catheter.

An advantage of the present invention is that the rotational oscillation provided by the motor shaft to the support catheter aids in longitudinally advancing the guidewire through an occlusion in the blood vessel.

Another advantage of the present invention is that a longitudinal reciprocation may be applied to the motor coincident with the rotational oscillation, so as to both longitudinal reciprocate and rotational oscillate the support catheter in the blood vessel.

BRIEF DESCRIPTION OF DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate at least one embodiment of the invention, and such exemplifications are not to be construed as limiting the scope of the invention in any manner.

DESCRIPTION OF EMBODIMENTS

Figure 1:
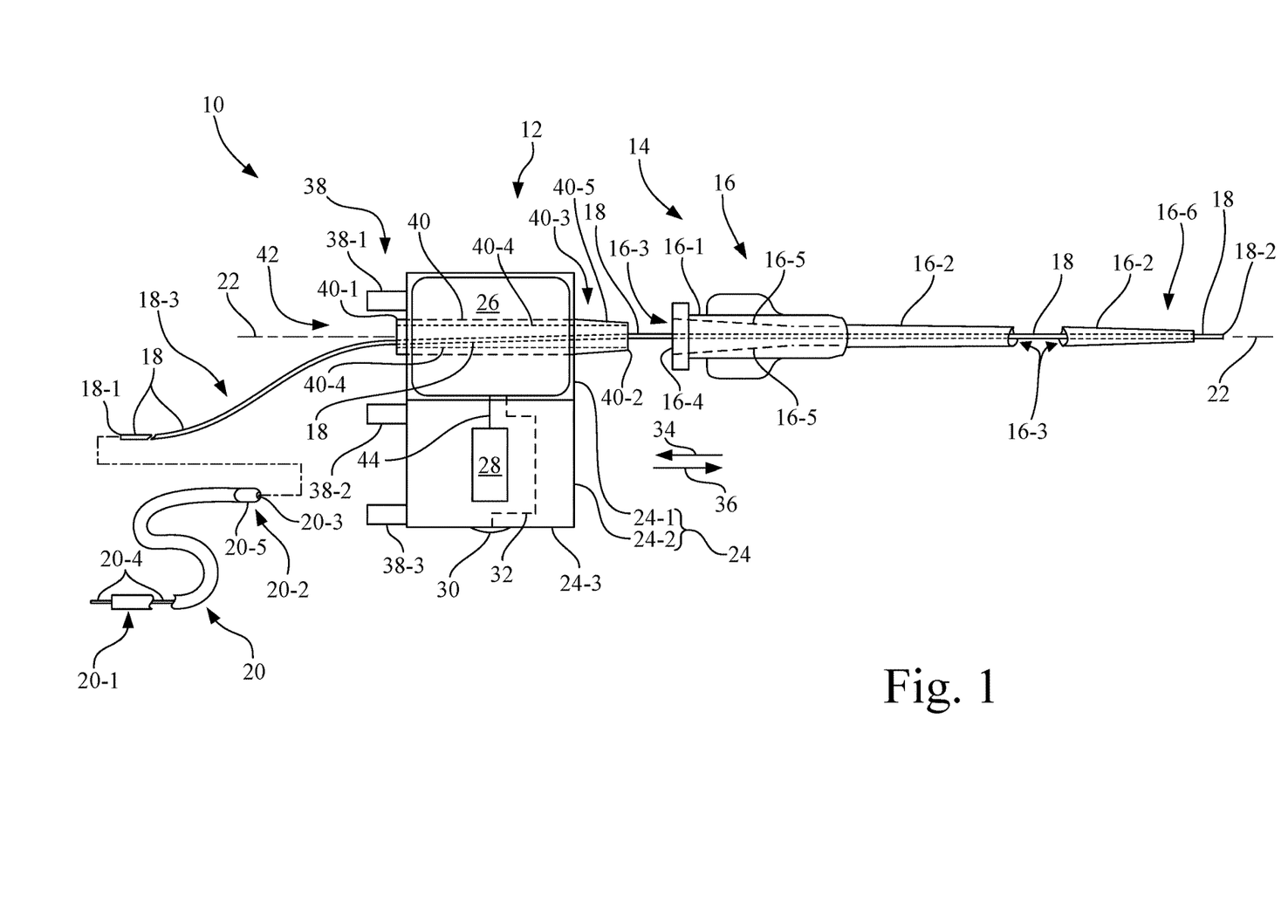
FIG. 1 is a diagrammatic illustration of a vascular device insertion system of the present invention, which includes a vascular device insertion apparatus and support catheter that may be used to aid in the insertion and placement of a guidewire and/or a vascular catheter.

Referring now to the drawings, and more particularly to FIG. 1, there is shown a vascular device insertion system 10 which generally includes a vascular device insertion apparatus 12 and a vascular device 14. Vascular device 14 may be, for example, a support catheter 16, and which may be accompanied by a guidewire 18 and/or a vascular catheter, such as for example, an ultrasonic catheter 20. In FIG. 1, vascular device 14 and support catheter 16 are arranged along a longitudinal axis 22.

Support catheter 16 includes a hub 16-1 and a flexible elongate member 16-2 that extends distally from hub 16-1. A catheter lumen 16-3 extends through hub 16-1 and flexible elongate member 16-2, i.e., through an entirety of the length of support catheter 16. Hub 16-1 includes a mounting aperture 16-4 that forms a proximal part of catheter lumen 16-3. Mounting aperture 16-4 of hub 16-1 has an enlarged diameter relative to the diameter of the remainder of catheter lumen 16-3, and in the present embodiment, mounting aperture 16-4 of hub 16-1 has a distally extending interior taper 16-5 (e.g., frustoconical). Flexible elongate member 16-2 has a distal end portion 16-6.

Guidewire 18 has a first end 18-1 and a second end 18-2. Guidewire 18 is typical of that known in the art, and may be, for example, a flexible metal cable or wire, such as a nitinol wire or cable.

In the embodiment of FIG. 1, the vascular catheter, which in the present embodiment is ultrasonic catheter 20, has a catheter proximal portion 20-1, a catheter distal portion 20-2, and a guidewire lumen 20-3. Guidewire lumen 20-3 is configured, e.g., in size and shape, to receive guidewire 18, such that the vascular catheter, e.g., ultrasonic catheter 20, may be guided to the region of interest by advancing the vascular catheter over guidewire 18 in a distal direction 36. In the present embodiment, ultrasonic catheter 20 may include a core wire 20-4 that is configured to transfer vibrational energy to a work head 20-5 at catheter distal portion 20-2.

Vascular device insertion apparatus 12 includes an insertion module housing 24, a motor 26, a motor controller 28, and a slider 30. Motor 26 and motor controller 28 may be battery operated, and the battery may be contained in insertion module housing 24.

Insertion module housing 24 includes a motor housing 24-1 and a base housing 24-2. Motor housing 24-1 of insertion module housing 24 may include a chamber that contains and mounts motor 26. Base housing 24-2 of insertion module housing 24 may include a chamber that contains and mounts motor controller 28.

Motor 26 is slidably mounted to motor housing 24-1 of insertion module housing 24, e.g., by rails, such that motor 26 is longitudinally movable along longitudinal axis 22 relative to insertion module housing 24. Slider 30 may be mounted to a side wall 24-3 of insertion module housing 24. Slider 30 is connected to motor 26 via a linkage 32, such that a longitudinal movement of slider 30 in a proximal direction 34 or distal direction 36 causes a corresponding longitudinal movement of motor 26 in proximal direction 34 or distal direction 36. Stated differently, slider 30 is configured to longitudinally reciprocate the motor 26 along longitudinal axis 22, i.e., to alternatingly move in proximal direction 34 and distal direction 36, by a reciprocating siding movement of slider 30 relative to insertion module housing 24.

Figure 2:
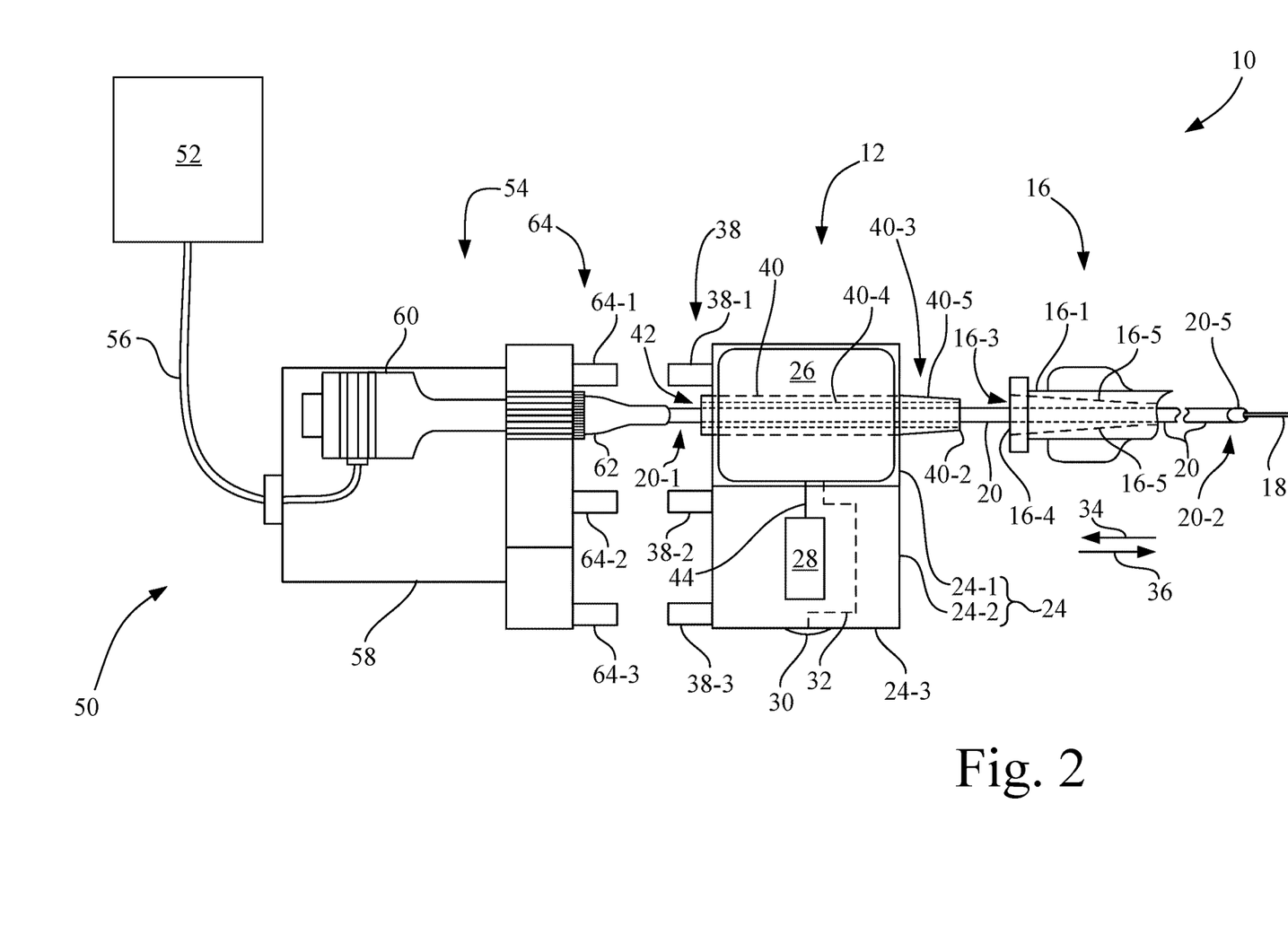
FIG. 2 is a diagrammatic illustration of the vascular device insertion system of FIG. 1, which includes an ultrasonic system that may be used in conjunction with, and coupled to, the vascular device insertion apparatus and the support catheter of FIG. 1.

Insertion module housing 24 may further include a plurality of mounting features 38 for connection to an auxiliary device, as depicted in FIG. 2. In the present embodiment, the plurality of mounting features 38 may be configured and arranged as a set of proximally extending posts, and the plurality of mounting features 38 may be magnetic. In the present embodiment, individual mounting features of the plurality of mounting features 38 are identified as mounting feature 38-1, mounting feature 38-2, and mounting feature 38-3.

Motor 26 may be, for example, a DC-motor, such as a stepper motor. Motor 26 has a hollow motor shaft 40 arranged along longitudinal axis 22. Hollow motor shaft 40 has a proximal end 40-1, a distal end 40-2, a distal end portion 40-3, and an elongate opening 40-4. Elongate opening 40-4 extends from proximal end 40-1 to distal end 40-2 along longitudinal axis 22. Stated differently, elongate opening 40-4 extends through an entirety of the length of hollow motor shaft 40. In the present embodiment, for example, elongate opening 40-4 may have the shape of a cylinder through an entirety of the length of hollow motor shaft 40.

Distal end portion 40-3 of hollow motor shaft 40 is configured to couple to hub 16-1 of support catheter 16. In the present embodiment, hollow motor shaft 40 has a distally extending exterior taper 40-5 that is sized and shaped to engage the distally extending interior taper 16-5 of hub 16-1 of support catheter 16 in a friction fit, so as to releasably connect hollow motor shaft 40 of motor 26 to hub 16-1 of support catheter 16.

When distal end portion 40-3 of hollow motor shaft 40 is coupled to hub 16-1 of support catheter 16, then elongate opening 40-4 of hollow motor shaft 40 and catheter lumen 16-3 of support catheter 16 together define a continuous passage 42 that longitudinally extends through the combination of support catheter 16 and hollow motor shaft 40 of motor 26. Guidewire 18 may be located in, e.g., advanced through, continuous passage 42 defined by elongate opening 40-4 in hollow motor shaft 40 and catheter lumen 16-3 of support catheter 16, wherein a first end portion 18-3 of guidewire 18 is proximal to proximal end 40-1 of hollow motor shaft 40. Continuous passage 42 is configured, e.g., in size and shape, such that guidewire 18 may be freely movable, e.g., longitudinally, in continuous passage 42 by manual manipulation of first end portion 18-3 of guidewire 18, such that second end 18-2 of guidewire 18 may distally extend from distal end portion 16-6 of support catheter 16. As used herein, the term "freely movable" means to encounter non-substantial resistance to movement, wherein substantial resistance will result in buckling or bending of the member being longitudinally moved.

Alternatively, or supplemental to guidewire 18, the vascular catheter, e.g., ultrasonic catheter 20, may be located in continuous passage 42 defined by elongate opening 40-4 in hollow motor shaft 40 and catheter lumen 16-3 of support catheter 16, wherein catheter proximal portion 20-1 of ultrasonic catheter 20 is proximal to proximal end 40-1 of hollow motor shaft 40. Continuous passage 42 is configured, e.g., in size and shape, such that ultrasonic catheter 20 is freely movable, e.g., longitudinally, in continuous passage 42 by manual manipulation of catheter proximal portion 20-1 of ultrasonic catheter 20, such that catheter distal portion 20-2 of ultrasonic catheter 20 may distally extend from distal end portion 16-6 of support catheter 16.

Motor controller 28 is electrically coupled to motor 26. For example, motor controller 28 may be electrically connected to motor 26 by an electrical cable 44. Motor controller 28 is configured, e.g., through hardwired or programmable logic, to control motor 26 so as to rotationally oscillate hollow motor shaft 40 about longitudinal axis 22, and to in turn rotationally oscillate support catheter 16, e.g., alternatingly clockwise to counterclockwise. In embodiments where motor 26 is a stepper motor, for example, then motor controller 28 will be a stepper motor controller.

In one embodiment, for example, the rotational oscillation of hollow motor shaft 40 may be less than one full revolution of hollow motor shaft 40, and optionally, may be variable as to the rotational extent. For example, the rotational oscillation of hollow motor shaft 40 may be variable between one-eighth revolution and one-half revolution, alternating between clockwise and counterclockwise rotational directions. In turn, support catheter 16 will also rotationally oscillate in accordance with the rotational oscillation of hollow motor shaft 40.

While hollow motor shaft 40 of motor 26 and support catheter 16 are rotationally oscillated by motor 26 and/or longitudinally reciprocated by slider 30, guidewire 18 may be manually manipulated and advanced by the user through continuous passage 42 formed by elongate opening 40-4 in hollow motor shaft 40 and catheter lumen 16-3 of support catheter 16. For example, in a vascular procedure, the rotational oscillation and/or longitudinal reciprocation of distal end portion 16-6 of flexible elongate member 16-2 of support catheter 16 is intended to help advance second end 18-2 of guidewire 18 to pass through and extend beyond a vascular occlusion (partial or total) in a blood vessel.

Alternatively, or supplemental to guidewire 18, the vascular catheter, such as ultrasonic catheter 20, may be manually manipulated and advanced by the user through continuous passage 42 formed by elongate opening 40-4 in hollow motor shaft 40 and catheter lumen 16-3 of support catheter 16. For example, in a vascular procedure, the rotational oscillation and/or longitudinal reciprocation of distal end portion 16-6 of flexible elongate member 16-2 of support catheter 16 may be used to help the user manually longitudinally advance work head 20-5 of catheter distal portion 20-2 of ultrasonic catheter 20 into engagement with, and to pass through, a vascular occlusion (partial or total) in a blood vessel.

Referring also to FIG. 2, there is shown the vascular device insertion system 10 configured to include an ultrasonic system 50. Ultrasonic system 50 includes an ultrasonic signal generator 52 and an ultrasonic device 54.

Ultrasonic signal generator 52 is typical of that known in the art, and may be configured to generate an ultrasonic electrical signal in the form of an ultrasonic excitation signal, e.g., in a frequency range of 20 kHz-40 kHz, that is supplied to ultrasonic device 54 via an excitation signal cable 56.

In the present embodiment, ultrasonic device 54 includes a device housing 58, an ultrasonic transducer 60, and ultrasonic catheter 20. Core wire 20-4 (see FIG. 1) of catheter proximal portion 20-1 of ultrasonic catheter 20 is operatively coupled to ultrasonic transducer 60, e.g., via a sonic coupler 62. Device housing 58 contains ultrasonic transducer 60, which is mounted internally to device housing 58. Device housing 58 may be constructed as a handpiece configured to be held by a user, such as for example, wherein device housing 58 has an outer shape and size to facilitate being grasped by the user during a medical procedure, such as for example, a vascular occlusion related procedure.

Ultrasonic transducer 60 may be, for example, a piezoelectric-type transducer. Ultrasonic transducer 60 of ultrasonic device 54 is electrically connected to ultrasonic signal generator 52 by excitation signal cable 56, and ultrasonic transducer 60 is configured to receive and convert the ultrasonic excitation signal generated by ultrasonic signal generator 52 into ultrasonic vibrational energy, which may be in a frequency range corresponding to that of the ultrasonic excitation signal generated by ultrasonic signal generator 52. For example, if the frequency of the ultrasonic excitation signal generated by ultrasonic signal generator 52 and supplied to ultrasonic transducer 60 is 20 kHz, then the vibrational frequency of the output of ultrasonic transducer 60 correspondingly may be 20 kHz, which in turn is supplied to core wire 20-4 (see FIG. 1) of ultrasonic catheter 20. As more fully described above with respect to FIG. 1, continuous passage 42 of vascular device insertion apparatus 12 is configured such that ultrasonic catheter 20 is movable in continuous passage 42 to distally extend from support catheter 16.

Device housing 58 includes a plurality of mounting features 64. The plurality of mounting features 64 of device housing 58 is configured to releasably connect to the plurality of mounting features 38 insertion module housing 24, so as to releasably mount device housing 58 to insertion module housing 24. In the present embodiment, the plurality of mounting features 64 may be configured and arranged as a set of proximally extending posts or post receptacles (e.g., apertures). In the present embodiment, individual mounting features of the plurality of mounting features 64 are identified as mounting feature 64-1, mounting feature 64-2, and mounting feature 64-3, which are configured (e.g., in size, shape, and function) to releasably connect to mounting feature 38-1, mounting feature 38-2, and mounting feature 38-3, respectively, of insertion module housing 24.

In one embodiment, for example, the plurality of mounting features 38 of insertion module housing 24 and the plurality of mounting features 64 of device housing 58 may be configured and arranged to couple together by magnetic attraction. In one implementation, for example, the opposing pairs (e.g., mounting feature 38-1 paired with mounting feature 64-1) of each of the plurality of mounting features 38 of insertion module housing 24 and the plurality of mounting features 64 of device housing 58 may be a magnet, such that the magnetic attraction is by a North Pole/South Pole magnetic arrangement, so as to facilitate the magnetic coupling of device housing 58 of ultrasonic device 54 to insertion module housing 24 of vascular device insertion apparatus 12. In another implementation, for example, one of the mounting features of the opposed pairs of mounting features (e.g., mounting feature 38-1 paired with mounting feature 64-1) may be magnetic while the other is (or includes) a magnetic material, such as iron, so as to facilitate the magnetic coupling of device housing 58 of ultrasonic device 54 to insertion module housing 24 of vascular device insertion apparatus 12.

As device housing 58 is moved into engagement with insertion module housing 24, ultrasonic catheter 20 longitudinally moves in continuous passage 42, e.g., through elongate opening 40-4 of hollow motor shaft 40 and catheter lumen 16-3 of support catheter 16, is longitudinally moved in distal direction 36. In embodiments that include guidewire 18 in continuous passage 42, then guidewire 18 may be received in guidewire lumen 20-3 (see FIG. 1) of ultrasonic catheter 20, such that ultrasonic catheter 20 moves distally through continuous passage 42 along guidewire 18 as ultrasonic catheter 20 is moved longitudinally in distal direction 36.

The operation of vascular device insertion apparatus 12, as depicted in FIG. 1, will now be described with respect to a vascular procedure to locate guidewire 18 in a blood vessel of a patient. Support catheter 16 is connected to hollow motor shaft 40 of motor 26, so as to establish continuous passage 42 of vascular device insertion system 10. Support catheter 16 is inserted into a blood vessel of the patient, followed by the threading of guidewire 18 into elongate opening 40-4 (of hollow motor shaft 40) that forms the initial portion of continuous passage 42 of vascular device insertion system 10. Motor 26 is then actuated by motor controller 28 so that hollow motor shaft 40 of motor 26 and support catheter 16 (including distal end portion 16-6 of flexible elongate member 16-2 of support catheter 16) are rotationally oscillated, in unison, so as to aid in the distal advancement of support catheter 16 through the blood vessel to the vascular occlusion site. Optionally, motor 26 and support catheter 16 also may be longitudinally displaced, e.g., reciprocated, by slider 30, alone or in combination with the rotational oscillation. While hollow motor shaft 40 of motor 26 and support catheter 16 are rotationally oscillated, guidewire 18 is manually manipulated and advanced by the physician through the continuous passage 42 formed by elongate opening 40-4 in hollow motor shaft 40 and catheter lumen 16-3 of support catheter 16, and second end 18-2 of guidewire 18 is advanced into engagement with the vascular occlusion in the blood vessel. The rotational oscillation and/or longitudinal reciprocation of distal end portion 16-6 of flexible elongate member 16-2 of support catheter 16 helps the physician to further advance second end 18-2 of guidewire 18 to pass through and extend beyond a vascular occlusion (partial or total) in the blood vessel.

With reference to FIGS. 1 and 2, after guidewire 18 is placed at the desired location in the blood vessel of the patient, first end 18-1 of guidewire 18 may then be threaded into and through guidewire lumen 20-3 of ultrasonic catheter 20 of ultrasonic device 54, such that ultrasonic catheter 20 may be advanced distally through continuous passage 42 along guidewire 18 as ultrasonic catheter 20 is moved longitudinally in distal direction 36. Ultrasonic signal generator 52 may then be energized to send the ultrasonic excitation signal to ultrasonic transducer 60. Ultrasonic transducer 60 receives and converts the ultrasonic excitation signal into ultrasonic vibrational energy, which in turn is supplied to core wire 20-4 (see FIG. 1) of ultrasonic catheter 20 so as to transmit vibrational energy to work head 20-5 which engages and bores into a proximal cap of the vascular occlusion.

While in some of the examples and embodiments above the structure and operation of vascular device insertion apparatus 12 has been described in terms of aiding insertion of a guidewire 18 in a blood vessel to a desired location, e.g., so as to guide the positioning of a vascular catheter, such as ultrasonic catheter 20, it is to be understood that in some procedures vascular device insertion apparatus 12 may be used to aid in directly inserting the vascular catheter to a desired location in the blood vessel without using guidewire 18, if desired.

The following items also relate to the invention:

In one form, the invention relates to a vascular device insertion system, which may be configured to advance a support catheter in a vessel to facilitate the positioning of an auxiliary device, such as a guidewire and/or an ultrasonic catheter. The system may comprise a support catheter that has a hub, a flexible elongate member that extends distally from the hub, and a catheter lumen that extends through the hub and the flexible elongate member. The support catheter may be arranged along a longitudinal axis. The system also may comprise an insertion module housing that may (be configured to) contain a motor that has a hollow motor shaft arranged along a longitudinal axis. In other words, the system may comprise the motor. The hollow motor shaft has a proximal end, a distal end, a distal end portion, and an elongate opening that may extend from the proximal end to the distal end along the longitudinal axis. The distal end portion of the hollow motor shaft may be configured to couple, e.g., in a direct connection, to the hub of the support catheter. The elongate opening of the hollow motor shaft and the catheter lumen of the support catheter together define a continuous passage. A motor controller may be electrically coupled to the motor. The motor controller may be configured to control the motor so as to rotationally oscillate the hollow motor shaft about the longitudinal axis, and to in turn rotationally oscillate the support catheter. Hence, the system is configured such that the motor may (be configured to) rotationally oscillate the hollow motor shaft about the longitudinal axis, and in turn rotationally oscillate the support catheter. In other words, the hollow motor shaft and the support catheter may be (configured to be) rotationally oscillated in unison around the (common) longitudinal axis, by the motor.

In some embodiments, a slider may be coupled to the motor. The slider may be configured to longitudinally reciprocate the motor along the longitudinal axis.

In some embodiments, the system may be configured to facilitate a positioning of a guidewire. The guidewire has a first end and a second end. The guidewire may be located in the continuous passage defined by the elongate opening in the hollow motor shaft and the catheter lumen of the support catheter, wherein a first end portion of the guidewire may be proximal to the proximal end of the hollow motor shaft. The continuous passage may be configured such that the guidewire may be manually movable in the continuous passage to distally extend from the support catheter.

In some embodiments, the system may comprise an ultrasonic catheter that has a catheter proximal portion and a catheter distal portion. The ultrasonic catheter may be located in the continuous passage defined by the elongate opening in the hollow motor shaft and the catheter lumen of the support catheter, wherein the catheter proximal portion of the ultrasonic catheter may be proximal to the proximal end of the hollow motor shaft. The continuous passage may be configured such that the ultrasonic catheter may be movable in the continuous passage to distally extend from the support catheter.

In embodiments that include the ultrasonic catheter, the ultrasonic catheter may include a guidewire lumen configured to receive the guidewire.

In some embodiments, the system may comprise an ultrasonic device. The ultrasonic device may comprise an ultrasonic transducer, a device housing configured to contain the ultrasonic transducer, and an ultrasonic catheter that has a catheter proximal portion and a catheter distal portion. The catheter proximal portion may be operatively coupled to the ultrasonic transducer. The continuous passage may be configured such that the ultrasonic catheter may be movable in the continuous passage to distally extend from the support catheter.

In the embodiment of the previous paragraph, the ultrasonic catheter may have a guidewire lumen configured to receive a guidewire. The system may be configured such that the ultrasonic catheter may be guided through the continuous passage along the guidewire as the ultrasonic catheter is moved in a distal direction over the guidewire.

In the embodiments that include the insertion module housing and the device housing, the insertion module housing may include a first plurality of mounting features and the device housing may include a second plurality of mounting features. The first plurality of mounting features may be configured to releasably connect to the second plurality of mounting features to mount the device housing to the insertion module housing. The system may be configured such that the first plurality of mounting features may be configured to releasably connect to the second plurality of mounting features to mount the device housing to the insertion module housing.

In the embodiment of the previous paragraph, the first plurality of mounting features of the insertion module housing and the second plurality of mounting features of the device housing may be configured to form a magnetic connection, e.g., may be magnetic.

In some embodiments that include an ultrasonic transducer as a part of the system, the system may comprise an ultrasonic signal generator that may be electrically coupled to the ultrasonic transducer. The ultrasonic signal generator may be configured to supply an electrical excitation signal to the ultrasonic transducer.

In another form, the invention relates to a vascular device insertion system that may comprise a support catheter that has a hub, a flexible elongate member that extends distally from the hub, and a catheter lumen that extends through the hub and the flexible elongate member. An insertion module housing may be configured to contain a motor that has a hollow motor shaft arranged along a longitudinal axis. The hollow motor shaft has a proximal end, a distal end, a distal end portion, and an elongate opening that may extend from the proximal end to the distal end along the longitudinal axis. The distal end portion of the hollow motor shaft may be configured to couple to the hub of the support catheter. The elongate opening of the hollow motor shaft and the catheter lumen of the support catheter together define a continuous passage. A guidewire has a first end and a second end, therein the guidewire may be located in the continuous passage defined by the elongate opening in the hollow motor shaft and the catheter lumen of the support catheter. A first end portion of the guidewire may be proximal to the proximal end of the hollow motor shaft. The continuous passage may be configured such that the guidewire may be freely manually movable in the continuous passage by manual manipulation of the first end portion of the guidewire. A motor controller may be electrically coupled to the motor. The motor controller may be configured to rotationally oscillate the hollow motor shaft about the longitudinal axis to in turn rotationally oscillate the support catheter. The features of preceding embodiments also apply to this form of the invention.

In some embodiments, a slider may be coupled to the motor, wherein the slider may be configured to longitudinally reciprocate the motor along the longitudinal axis.

In some embodiments, the system may comprise an ultrasonic device that may comprise an ultrasonic transducer, a device housing configured to contain the ultrasonic transducer, and an ultrasonic catheter that has a catheter proximal portion, a catheter distal portion, and a guidewire lumen. The catheter proximal portion may be operatively coupled to the ultrasonic transducer. The guidewire lumen may be configured to receive the guidewire. The system may be configured such that the ultrasonic catheter longitudinally moves in the continuous passage along the guidewire when the ultrasonic catheter is longitudinally moved.

In any of the embodiments that has the insertion module housing and the device housing, the insertion module housing may include a first plurality of mounting features and the device housing may include a second plurality of mounting features. The first plurality of mounting features may be configured to releasably connect to the second plurality of mounting features to mount the device housing to the insertion module housing.

In the embodiment according to the previous paragraph, the first plurality of mounting features of the insertion module housing and the second plurality of mounting features of the device housing may be configured to form a magnetic connection, e.g., may be magnetic.

In any of the embodiments that has the device housing, the device housing may be a handpiece configured to be held by a user.

In any of the embodiments that includes the ultrasonic transducer, the system may comprise an ultrasonic signal generator that may be electrically coupled to the ultrasonic transducer. The ultrasonic signal generator may be configured to supply an electrical excitation signal to the ultrasonic transducer.

In another form, the invention relates to a vascular device insertion apparatus that may be configured for (use in) advancing a support catheter and a guide wire in a vessel. The support catheter may have a hub, a flexible elongate member that extends distally from the hub, and a catheter lumen that extends through the hub and the flexible elongate member. The vascular device insertion apparatus may comprise an insertion module housing that is configured to contain a motor that has a hollow motor shaft arranged along a longitudinal axis. The hollow motor shaft may have a proximal end, a distal end, a distal end portion, and an elongate opening that may extend from the proximal end to the distal end along the longitudinal axis. The distal end portion of the hollow motor shaft may be configured to couple to the hub of the support catheter, wherein the elongate opening of the hollow motor shaft and the catheter lumen of the support catheter together define a continuous passage. The continuous passage may be configured to receive the guidewire. A motor controller may be electrically coupled to the motor. The motor controller may be configured to rotationally oscillate the hollow motor shaft about the longitudinal axis to in turn rotationally oscillate the support catheter. This form of the invention is directed to the vascular device insertion system of preceding embodiments, wherein the continuous passage may be configured to receive the guidewire. The features of these preceding embodiments also apply to this form of the invention.

In some embodiments, a slider may be coupled to the motor. The slider may be configured to longitudinally reciprocate the motor along the longitudinal axis.

In any of the embodiments, the insertion module housing may optionally include a plurality of mounting features configured to mount to a device housing of an ultrasonic transducer.

As used herein, words of degree are relative modifiers intended to indicate permissible variation from the characteristic so modified. Such terms are not intended to be limited to the absolute value of the characteristic which it modifies, but rather possessing more of the physical or functional characteristic than the opposite While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A vascular device insertion system, comprising:
    a support catheter having a hub, a flexible elongate member that extends distally from the hub, and a catheter lumen that extends through the hub and the flexible elongate member;
    an insertion module housing configured to contain a motor having a hollow motor shaft arranged along a longitudinal axis, the hollow motor shaft having a proximal end, a distal end, a distal end portion, and an elongate opening that extends from the proximal end to the distal end along the longitudinal axis, the distal end portion of the hollow motor shaft configured to couple to the hub of the support catheter, and wherein the elongate opening of the hollow motor shaft and the catheter lumen of the support catheter together define a continuous passage; and
    a motor controller electrically coupled to the motor, the motor controller configured to control the motor so as to rotationally oscillate the hollow motor shaft about the longitudinal axis, and to in turn rotationally oscillate the support catheter.

2. The system according to claim 1, comprising a slider coupled to the motor, the slider configured to longitudinally reciprocate the motor along the longitudinal axis.

3. The system according to claim 1, comprising a guidewire having a first end and a second end, the guidewire being located in the continuous passage defined by the elongate opening in the hollow motor shaft and the catheter lumen of the support catheter, wherein a first end portion of the guidewire is proximal to the proximal end of the hollow motor shaft, and the continuous passage configured such that the guidewire is manually movable in the continuous passage to distally extend from the support catheter.

4. The system according to claim 1, comprising an ultrasonic catheter having a catheter proximal portion and a catheter distal portion, the ultrasonic catheter being located in the continuous passage defined by the elongate opening in the hollow motor shaft and the catheter lumen of the support catheter, wherein the catheter proximal portion of the ultrasonic catheter is proximal to the proximal end of the hollow motor shaft, and the continuous passage configured such that the ultrasonic catheter is movable in the continuous passage to distally extend from the support catheter.

5. The system according to claim 4, wherein the ultrasonic catheter includes a guidewire lumen configured to receive the guidewire.

6. The system according to claim 1, further comprising an ultrasonic device, comprising:
    an ultrasonic transducer;
    a device housing configured to contain the ultrasonic transducer; and
    an ultrasonic catheter having a catheter proximal portion and a catheter distal portion, the catheter proximal portion being operatively coupled to the ultrasonic transducer,
    wherein the continuous passage is configured such that the ultrasonic catheter is movable in the continuous passage to distally extend from the support catheter.

7. The system according to claim 6, wherein the ultrasonic catheter has a guidewire lumen configured to receive a guidewire, the system configured such that the ultrasonic catheter is guided through the continuous passage along the guidewire as the ultrasonic catheter is moved in a distal direction over the guidewire.

8. The system according to claim 6, wherein:
    the insertion module housing includes a first plurality of mounting features; and
    the device housing includes a second plurality of mounting features,
    wherein the first plurality of mounting features is configured to releasably connect to the second plurality of mounting features to mount the device housing to the insertion module housing.

9. The system according to claim 8, wherein the first plurality of mounting features of the insertion module housing and the second plurality of mounting features of the device housing are magnetic.

10. The system according to claim 6, further comprising an ultrasonic signal generator electrically coupled to the ultrasonic transducer, the ultrasonic signal generator configured to supply an electrical excitation signal to the ultrasonic transducer.

11. A vascular device insertion system, comprising:
    a support catheter having a hub, a flexible elongate member that extends distally from the hub, and a catheter lumen that extends through the hub and the flexible elongate member;
    an insertion module housing configured to contain a motor having a hollow motor shaft arranged along a longitudinal axis, the hollow motor shaft having a proximal end, a distal end, a distal end portion, and an elongate opening that extends from the proximal end to the distal end along the longitudinal axis, the distal end portion of the hollow motor shaft configured to couple to the hub of the support catheter, and wherein the elongate opening of the hollow motor shaft and the catheter lumen of the support catheter together define a continuous passage;
    a guidewire having a first end and a second end, the guidewire being located in the continuous passage defined by the elongate opening in the hollow motor shaft and the catheter lumen of the support catheter, wherein a first end portion of the guidewire is proximal to the proximal end of the hollow motor shaft, and the continuous passage configured such that the guidewire is freely manually movable in the continuous passage by manual manipulation of the first end portion of the guidewire; and
    a motor controller electrically coupled to the motor, the motor controller configured to rotationally oscillate the hollow motor shaft about the longitudinal axis to in turn rotationally oscillate the support catheter.

12. The system according to claim 11, comprising a slider coupled to the motor, the slider configured to longitudinally reciprocate the motor along the longitudinal axis.

13. The system according to claim 11, further comprising an ultrasonic device, comprising:
    an ultrasonic transducer;
    a device housing configured to contain the ultrasonic transducer; and
    an ultrasonic catheter having a catheter proximal portion, a catheter distal portion, and a guidewire lumen, the catheter proximal portion being operatively coupled to the ultrasonic transducer, the guidewire lumen configured to receive the guidewire;

the system configured such that the ultrasonic catheter longitudinally moves in the continuous passage along the guidewire when the ultrasonic catheter is longitudinally moved.

14. The system according to claim 13, wherein:
the insertion module housing includes a first plurality of mounting features; and
the device housing includes a second plurality of mounting features,
wherein the first plurality of mounting features are configured to releasably connect to the second plurality of mounting features to mount the device housing to the insertion module housing.

15. The system according to claim 14, wherein the first plurality of mounting features of the insertion module housing and the second plurality of mounting features of the device housing are magnetic.

16. The system according to claim 13, wherein the device housing is a handpiece configured to be held by a user.

17. The system according to claim 13, further comprising an ultrasonic signal generator electrically coupled to the ultrasonic transducer, the ultrasonic signal generator configured to supply an electrical excitation signal to the ultrasonic transducer.

18. A vascular device insertion apparatus for use in advancing a support catheter and a guide wire in a vessel, the support catheter having a hub, a flexible elongate member that extends distally from the hub, and a catheter lumen that extends through the hub and the flexible elongate member, the vascular device insertion apparatus comprising:
an insertion module housing configured to contain a motor having a hollow motor shaft arranged along a longitudinal axis, the hollow motor shaft having a proximal end, a distal end, a distal end portion, and an elongate opening that extends from the proximal end to the distal end along the longitudinal axis, the distal end portion of the hollow motor shaft configured to couple to the hub of the support catheter, wherein the elongate opening of the hollow motor shaft and the catheter lumen of the support catheter together define a continuous passage, and the continuous passage is configured to receive the guidewire; and
a motor controller electrically coupled to the motor, the motor controller configured to rotationally oscillate the hollow motor shaft about the longitudinal axis to in turn rotationally oscillate the support catheter.

19. The vascular device insertion apparatus according to claim 18, comprising a slider coupled to the motor, the slider configured to longitudinally reciprocate the motor along the longitudinal axis.

20. The vascular device insertion apparatus according to claim 18, wherein the insertion module housing includes a plurality of mounting features configured to mount to a device housing of an ultrasonic transducer.

* * * * *